United States Patent [19]

Failli et al.

[11] 4,252,795

[45] Feb. 24, 1981

[54] N-SUBSTITUTED DIMERIC CYCLOPEPTIDE DERIVATIVES AND PREPARATION THEREOF

[75] Inventors: Amedeo Failli, St. Laurent; Hans U. Immer, Mount Royal; Manfred K. Götz, Hudson, all of Canada

[73] Assignee: Ayerst McKenna and Harrison Inc., Montreal, Canada

[21] Appl. No.: 941,532

[22] Filed: Sep. 11, 1978

[51] Int. Cl.³ .................... A61K 37/00; C07C 103/52
[52] U.S. Cl. .......................... 424/177; 260/112.5 R; 424/14; 424/365
[58] Field of Search .................. 260/112.5 R; 424/177

[56] References Cited

PUBLICATIONS

Degering, Organic Chemistry, 1951, pp. 145–147, 151 and 152.
Synthetic Org. Chem., 5/1953, pp. 412–415, 605 and 813.
Organic Chemistry, 1956, 2nd edition, pp. 413–416.

Primary Examiner—Dale R. Ore
Attorney, Agent, or Firm—Arthur E. Wilfond

[57] ABSTRACT

The N-substituted dimeric cyclopeptide derivatives of formula

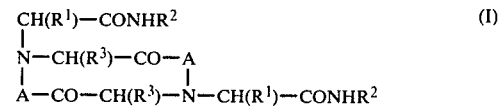

in which A is a peptide residue having one to four amino acid residues; $R^1$ is lower alkyl, phenyl or pheny(lower) alkylene; $R^2$ is lower alkyl, cyclo(lower)alkyl or lower alkoxycarbonyl(lower)alkylene; $R^3$ is a neutral amino acid side chain and a method for the preparation of the compounds of formula I are disclosed. The compounds of formula I are useful for treating microbial infections. Pharmaceutical compositions also are disclosed.

3 Claims, No Drawings

N-SUBSTITUTED DIMERIC CYCLOPEPTIDE DERIVATIVES AND PREPARATION THEREOF

BACKGROUND OF THE INVENTION (a) Field of Invention

The present invention relates to N-substituted dimeric cyclopeptide derivatives with antimicrobial activity and to a process for their preparation.

(b) Description of the Prior Art

A number of cyclic peptides have been either isolated from natural sources or prepared by classical synthetic methods, for example, see the review by E. Schrödes and K. L. Lübke, "The Peptides"; Vol. II; Academic Press, New York, 1966, pp 424–478.

The present invention discloses novel dimeric cyclopeptide derivatives in which two nitrogen atoms of the peptide back bone are substituted. These compounds have been found to have the desirable attributes of useful antimicrobial activity coupled with a low order of toxicity.

In addition, a novel process for preparing N-substituted dimeric cyclopeptide derivatives is disclosed.

SUMMARY OF THE INVENTION

The N-substituted dimeric cyclopeptide derivatives of this invention are represented as the compounds of formula I

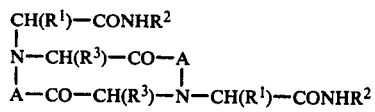

in which A is a peptide residue having one to four neutral amino acid residues; $R^1$ is lower alkyl, phenyl or phenyl(lower)alkylene; $R^2$ is lower alkyl, cyclo(lower)alkyl or lower alkoxycarbonyl(lower)alkylene; and $R^3$ is a neutral amino acid side chain.

A preferred group of N-substituted dimeric cyclopeptide derivatives of this invention are represented by formula I in which A is a peptide residue having one to four neutral amino acid residues wherein said neutral amino acid residues have a neutral side chain selected from hydrogen or lower alkyl; $R^1$ is lower alkyl, phenyl or phenyl(lower)alkylene; $R^2$ is lower alkyl, cyclo(lower)alkyl or lower alkoxycarbonyl(lower)alkylene; and $R^3$ is a neutral amino acid side chain selected from hydrogen or lower alkyl.

Another preferred group of N-substituted dimeric cyclopeptide derivatives of this invention are represented by formula I in which A is a peptide residue having two neutral amino acid residues wherein said neutral amino acid residues have a neutral side chain selected from hydrogen or lower alkyl; $R^1$ is lower alkyl, phenyl or phenyl(lower)alkylene; $R^2$ is lower alkyl, cyclo(lower)alkyl or lower alkoxycarbonyl(lower)alkylene; and $R^3$ is a neutral amino acid side chain selected from hydrogen or lower alkyl.

Still another preferred group of N-substituted dimeric cyclopeptide derivatives of this invention are represented by formula I in which A is Gly-Gly; $R^1$ is lower alkyl, phenyl or phenyl(lower)alkylene; $R^2$ is lower alkyl, cyclo(lower)alkyl or lower alkoxycarbonyl(lower)alkylene; and $R^3$ is hydrogen.

The compounds of formula 1 in which A, $R^1$, $R^2$ and $R^3$ are as defined herein are prepared by a process which comprises condensing together an aldehyde of formula $R^1$ CHO in which $R^1$ is as defined herein, an isonitrile of formula $R^2$ NC in which $R^2$ is as defined herein and a peptide of formula $H_2N-CH(R^3)-CO-A-OH$ in which A and $R^3$ are as defined herein.

The compounds of formula I form a pharmaceutical composition which comprises a compound of formula I and a pharmaceutically acceptable carrier.

The compounds of formula I are useful treating microbial infections in a mammal by administering to the mammal an antimicrobial effective amount of a compound of formula I.

DETAILS OF THE INVENTION

The term "lower alkyl" as used herein means straight chain alkyl radicals containing from one to six carbon atoms and branched chain alkyl radicals containing three or four carbon atoms and includes methyl, ethyl, propyl, isopropyl, butyl, isobutyl, pentyl, hexyl and the like.

The term "lower alkoxy" as used herein means straight chain alkoxy radicals containing from one to six carbon atoms and branched chain alkoxy radicals containing three or four carbon atoms and includes methoxy, ethoxy, isopropoxy, butoxy, hexanoxy and the like.

The term "cyclo(lower)alkyl" as used herein means saturated cyclic hydrocarbon radicals containing from three to six carbon atoms and includes cyclopropyl, cyclobutyl, cyclopentyl and cyclohexyl.

The term "(lower)alkylene" as used herein means a divalent organic radical derived from both straight and branched chain aliphatic hydrocarbons containing from one to six carbon atoms by removal of two hydrogen atoms and includes methylene, ethylene, butylene, 2-methyl-propylene, and the like.

The term "organic proton acceptor" as used herein includes triethylamine, N-ethylmorpholine, N-ethyl-diisopropylamine and the like.

The terms "amino acid" and "amino acid residue" as used herein means the common amino acids and amino acid residues having a neutral side chain and includes alanine, asparagine, cysteine, glycine, tryptophan, methionine, serine, tyrosine, valine, leucine, phenylalanine, isoleucine, proline, threonine and the like. The preferred amino acids and amino acid residues are selected from the common amino acids and amino acid residues having a neutral side chain selected from hydrogen or lower alkyl, and includes glycine, alanine, valine, leucine, isoleucine and the like.

In general the abbreviations used herein for designating the amino acids and the protective groups are based on recommendations of the IUPAC-IUB Commission on Biochemical Nomenclature, see Biochemistry, 11, 1732(1972). For instance Ala, Leu and Gly represent "residue" of L-alanine, L-leucine and glycine, respectively. The term "residue" means a radical derived from the corresponding L-amino acid by eliminating the hydroxy portion of the carboxy group and a hydrogen of the α-amino group. The term "amino acid side chain" is that part of a common neutral amino acid exclusive of the $-CH(NH_2)COOH$ portion, as defined by K. D. Kopple, "Peptides and Amino Acids", W. A. Benjamin Inc., New York and Amsterdam, 1966, pages 2 and 33. Examples of neutral amino acid side chains are $-CH_2CH(CH_3)_2$ (the side chain of leucine), $-H$(glycine), $-CH_3$(alanine), $-CH_2CONH_2$(asparagine), —CH₂SH(cysteine), 3-indolylmethylene(tryptophan), —CH₂CH₂SCH₃(methionine), —CH₂OH(serine), 4-hydroxybenzyl(tyrosine), —CH(CH₃)₂(valine), benzyl(phenylalanine), —CH(CH₃)C₂H₅(isoleucine), —CH(OH)CH₃(threonine) and the like. Note, therefore, that the term "amino acid side chain" includes hydrogen. The preferred neutral amino acid side chains are selected from hydrogen or lower alkyl and includes —H(the side chain of glycine), —CH₃(alanine), —CH(CH₃)₂(valine), —CH₂CH(CH₃)₂(leucine), —CH(CH₃)C₂H₅(isoleucine) and the like.

The amino acids and amino acid residues are all of the L configuration. It will be noted that the structures of the compounds of this invention include asymmetric carbon atoms. It is to be understood accordingly that the isomers arising from such asymmetry are included within the scope of this invention. Such isomers are obtained in substantially pure form by classical separation techniques and by sterically controlled synthesis and have arbitrarily been named as isomers L or M, respectively.

A number of procedures or techniques for the preparation of peptides have hitherto been well established and found in general textbooks of peptide chemistry; for example K. D. Kopple, supra, pp. 33–51 and E. Schröder and K. L. Lübke, "The Peptides"; Vol. 1; Academic Press, New York, 1965, pp. 3–128. For instance, the functional groups which are not involved in the peptide bond formation reaction are optionally protected by a protecting group or groups prior to the condensation reaction. Examples of protecting groups for an amino function of a peptide or amino acid not involved in the peptide bond formation are: the alkoxycarbonyls which include benzyloxycarbonyl (represented by Z), t-butoxycarbonyl (represented by Boc), α,α-dimethyl-3,5-dimethoxybenzyloxycarbonyl (represented by Ddz), 2-(p-biphenyl)-isopropyloxycarbonyl (represented by Bpoc), p-chlorobenzyloxycarbonyl, p-methoxybenzyloxycarbonyl, isopropyloxycarbonyl, or ethoxycarbonyl; the acyl type protecting groups which include formyl, trifluoroacetyl, phthalyl, acetyl (Ac), or toluenesulfonyl; the alkyl type protecting groups which include triphenylmethyl or trityl (represented by Trt) or benzyl; the preferred protecting groups used in the process of this invention are benzyloxycarbonyl, t-butoxycarbonyl, triphenylmethyl and α,α-dimethyl-3,5-dimethoxy-benzyloxycarbonyl. The carboxylic acid function of a peptide or amino acid can be considered protected by a lower alkyl or lower aralkyl ester which includes methyl (represented by OMe), ethyl (OEt), benzyl (OBzl) or tert-butyl (OBuᵗ) ester.

A peptide or amino acid is coupled with another peptide or amino acid to form a new peptide by the elimination of water (i.e. dehydrative coupling). More specifically, the OH portion of a free carboxyl group of a peptide or amino acid and the H portion of a free amino group of a peptide or amino acid are eliminated to form a new amide bond joining the peptide or amino acid starting materials. To promote facile condensation of a peptide free carboxyl group with a free amino group of another peptide to form a new peptide bond, the free carboxyl group must be activated. Descriptions of such carboxyl activating groups are included in the general textbooks of peptide chemistry by Kopple, or Schröder and Lübke, cited above. Examples of the activated form of a carboxyl are acid chloride, anhydride, azide, imidazolide, activated ester or O-acyl urea of a dialkylcarbodiimide (i.e. cyclohexylcarbodiimide).

The following activated esters have proved to be particularly suitable in the process of this invention: 2,4,5-trichlorophenyl (represented by OTcp), pentachlorophenyl (OPcp), p-nitrophenyl(ONp), or 1-benzotriazolyl; the succinimido derivative also is useful for this purpose.

The coupling of a peptide or amino acid having the activated carboxyl with the peptide or amino acid having a free amino group is conducted in an inert organic solvent at a temperature from −30° C. to about 50° C. For coupling to occur, the amino group must not be protonated. A sufficient amount of an organic proton acceptor is added to the above reaction mixture until the amino group is no longer protonated (usually pH 7.2 to 8.0).

The terms "peptide, dipeptide, tripeptide, and the like" used herein are not limited to refer to the respective parent peptides but also are used in reference to modified peptides which are functionalized or having protecting groups. The term "peptide" as used herein can be used in reference to a peptide with one to ten amino acid residues.

ANTIMICROBIAL ACTIVITY

The compounds of formula I exhibit utility as antimicrobial agents against a number of microorganisms, for example, bacteria, fungi and protozoa. The antibacterial and antifungal activity is demonstrated in standard tests, for example in those described in "Antiseptics, Disinfectants, Fungicides and Sterilization", G. F. Reddish, Ed., 2nd. ed., Lea and Febiger, Philadelphia, 1957 or by D. C. Grove and W. A. Randall in "Assay Methods of Antibiotics", Med. Encycl. Inc., [New York] 955. The antiprotozoic activity is demonstrated in standard tests, for example, see R. J. Schnitzer in "Experimental Chemotherapy," Vol. I. R. J. Schnitzer and F. Hawking, Ed., Academic Press, N.Y., 1963. p. 289.

The compounds are useful as antibacterial agents against pathogenic bacteria, for example, Klebsiella pneumoniae and Serratia marcescens and as antifungal agents against pathogenic fungi, for example, Candida albicans and Microsporum gypseum. In addition, the compounds exhibit utility as antiprotozoic agents against parasitic protozoa, for example, Trichomonas vaginalis.

For example, by employing a test like the serial broth dilution, see Grove and Randall, cited above, in which dilutions of the compounds of this invention in nutrient broth are inoculated with the microorganisms or fungi, described above, incubated at 37° C. for 2 days, respectively, and examined for the presence of growth, it may be shown that the preferred compounds N'N'-dicyclohexyl-α,α'-diisopropyl-2,5,8,11,14,17-hexaoxo-1,4,7,10,13,16-hexaazacyclooctadecane-1,10-diacetamide, isomer L, (Example 1), N'N'-dicyclohexyl-α,α'-diisopropyl-2,5,8,11,14,17-hexaoxo-1,4,7,10,13,16-hexaazacyclooctadecane-1,10-diacetamide, isomer M, (Example 1), and α,α'-diphenyl-N'N'-dicyclohexyl-2,5,8,11,14,17-hexaoxo-1,4,7,10,13,16-hexaazacyclooctadecane-1,10-diacetamide, isomer L, (Example 1) are able to inhibit growth totally in this system of Klebsiella pneumoniae and Serratia marcescens at a concentration of 100 mcg/ml.

When the compounds of this invention are employed as antimicrobial agents in a mammal they are used administered alone or in combination with pharmacologically acceptable carriers. The amount of the compound is determined by the solubility and chemical nature of the compound, chosen route of administration and standard biological practice. For example, the compounds may be administered orally in solid form containing such excipients as starch, milk sugar, certain types of clay and so forth. They may also be administered orally in the form of solutions or they may be injected parenterally. For parenteral administration they may be used in the form of a sterile solution containing other solutes, for example, enough saline or glucose to make the solution isotonic.

The dosage of the present therapeutic agents as antimicrobial agents will vary with the form of administration and the particular compound chosen. Furthermore, it will vary with the particular host under treatment. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford antimicrobially effective results without causing any harmful or deleterious side effects and preferably at a level that is in a range of from about 1.0 mg to about 500 mg per kilogram body weight per day, although as aforementioned variations will occur. However, a dosage level that is in the range of from about 10 mg to about 200 mg per kilogram body weight per day is most desirably employed in order to achieve effective results.

In addition, the compounds may be employed topically. For topical application they may be formulated in the form of solutions, creams, or lotions in pharmaceutically acceptable vehicles containing 0.1–5 percent, preferably 2 percent, of the agent and may be administered topically to the infected area of the skin.

Also the antibacterial properties of the compounds of this invention may be utilized for washing equipment in hospitals, homes and farms, instruments used in medicine and bacteriology, clothing used in bacteriological laboratories, and floors, walls and ceiling in rooms in which a background free of bacteria is desired. When employed in this manner the compounds of this invention may be formulated in a number of compositions comprising the active compound and an inert material. In such compositions, while the compounds of formula I of this invention may be employed in concentrations as low as 500 p.p.m., from a practical point of view, it is desirable to use from about 0.10 percent by weight, to about 5 percent by weight or more.

The formulations that may be used for antiseptic wash solutions of the compounds of this invention are varied and may readily be prepared by standard techniques, see for example, "Remington's Practice of Pharmacy," E. W. Martin et al., Eds., 12th ed., Mack Publishing Company, Easton, Pa., 1961, pp. 1,121–1,150. In general, the compounds may be made up in stock solutions. They can also be formulated as suspensions in an aqueous vehicle. These make useful mixtures for decontaminating premises. Also, aqueous vehicles containing emulsifying agents, such as sodium lauryl sulfate, and relatively high concentrations, e.g., up to about 5 percent by weight, of the compounds may be formulated by conventional techniques.

A typical antiseptic preparation useful for disinfecting floors, walls, ceiling, and articles in a contaminated room may be prepared by adding 5 to 25 g of a compound of this invention to a mixture of 150 to 300 g of polyethylene glycol 1,540 and 150 to 300 g of polyethylene glycol 300. The resulting mixture is stirred while a solution of 1 to 10 g of sodium lauryl sulfate in 300 to 400 ml of water is added portionwise. The article to be disinfected is coated or immersed in the preparation for a prolonged time, for example, one hour, and then rinsed with sterile water.

PROCESS

The starting materials required for the preparation of the compounds of formula I are aldehydes, isonitriles and peptides. These starting materials are either known or commercially available.

The aldehydes of formula $R^1$CHO are known and most are commercially available, for example, isobutyraldehyde and benzaldehyde, or are prepared by known methods, for example, see P. Karrer, "Organic Chemistry", 2nd. ed., Elsevier Publishing Co. Inc., New York, 1946, p. 149.

The isonitriles of formula $R^2$NC, are either known, namely, ethyl isocyanoacetate is described by R. Appel et al., Angew. Chem. Int. ed., 10 132 (1971) or are easily prepared by known methods, for example, by the methods described by P. Hoffmann, et al. in "Isonitrile Chemistry", Organic Chemistry, Vol. 20, I. Ugi. Ed., Academic Press, New York, 1971, p. 9.

The peptides of formula $H_2N$—CH($R^3$)—CO—A—OH are either known or commercially available, for example, glycyl-glycyl-glycine, or are prepared by known methods used in peptide chemistry.

The compounds of this invention are prepared by the following description of a preferred embodiment.

The practice of the preferred embodiment of the process of this invention involves the condensation of the following three starting materials; (1) an aldehyde of formula $R^1$CHO in which $R^1$ is lower alkyl, phenyl or phenyl(lower)alkylene; (2) an isonitrile of formula $R^2$NC in which $R^2$ is lower alkyl, cyclo(lower)alkyl or lower alkoxycarbonyl(lower)alkylene and (3) a peptide of formula $H_2N$—CH($R^3$)—CO—A—OH in which A is a peptide residue having one to four amino acid residues and $R^3$ is an amino acid side chain to obtain the corresponding compound of formula I

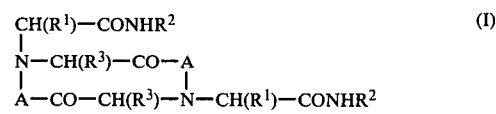

in which A, $R^1$, $R^2$ and $R^3$ are as defined herein.

The preferred N-substituted dimeric cyclopeptide derivatives of this invention are prepared by condensing the following three starting materials: (1) an aldehyde of formula $R^1$CHO in which $R^1$ is as defined herein, (2) an isonitrile of formula $R^2$NC in which $R^2$ is as defined herein and (3) a peptide of formula $H_2N$—CH($R^3$)—CO—A—OH in which A is Gly-Gly and $R^3$ is hydrogen to obtain the corresponding compound of formula I in which $R^1$ and $R^2$ are as defined herein, A is Gly-Gly and $R^3$ is hydrogen.

Although not critical, it is preferable to use approximately equimolar amounts of the isonitrile of formula $R^2$NC and the peptide of formula $H_2N$—CH($R^3$)—CO—A—OH and about one to five molar equivalents, preferably two to four molar equivalents, of the aldehyde of formula $R^1$CHO for this condensation. The condensation is effected most conveniently in a dry inert organic solvent, for example, dimethylformamide, dimethyl sulfoxide or in an aliphatic alkanol which includes methanol, can be selected from methanol and ethylene glycol.

The temperature and duration of the condensation are also not critical. The reaction may be performed at temperatures ranging from −20° to 100° C.; however, a range from 10° to 40° C. is most convenient. The reaction time can be varied, and depends on the reactivity of the various starting materials; however, reaction times from one hour to several days are employed generally, with ten hours to ten days being preferred.

The above condensation of the three starting materials requires the use of dilute solutions to counteract undesirable polymerization. Suitable and preferred concentrations of the reaction solution with respect to the isonitrile or peptide starting materials can range from 0.1 mmole per ml of solvent to 1.0 mmole per ml of solvent.

Some of the peptides of formula $H_2N-CH(R^3)-CO-A-OH$ may not be sufficiently soluble in the inert organic solvent selected for the condensation to give the corresponding compound of formula 1 in sufficient yield. A useful method to increase the solubility of the peptide starting material is to prepare the acid addition salt of the peptide starting material, for example, salts formed with one molar equivalent of hydrochloric acid or trifluoroacetic acid. The acid addition salt of the peptide starting material is employed in the condensation along with a corresponding amount of an organic proton acceptor, for example, triethylamine, N-methyl morpholine and the like.

Thereafter, the compound of formula I is isolated and purified according to standard procedures. For instance the product can be precipitated with a di(lower)alkyl ether or water and, if needed, purified by chromatography and crystallization.

It should be noted that the product formed is a mixture of two isomers. Separation of the isomers can be effected by chromatography. For example, chromatography using silica gel as the absorbent has been found to be effective for the separation.

The following examples illustrate further this invention.

EXAMPLE 1

N,N'-Dicyclohexyl-α,α'-diisopropyl-2,5,8,11,14,17-hexaoxo-1,4,7,10,13,16-hexaazacyclooctadecane-1,10-diacetamide (I; $R^1=CH(CH_3)_2$, $R^2$=cyclohexyl, $R^3$=H and A=Gly-Gly)

Cyclohexylisonitrile (0.97 g, 9 mmole) is added dropwise to a suspension at 0° to 5° C. of glycyl-glycyl-glycine (1.7 g, 9 mmole) and 2-methylpropanal (2.16 g, 30 mmole) in anhydrous ethylene glycol (15 ml). After the addition is complete, the suspension is stirred at room temperature for 5 days. Water is added and the precipitate is collected and washed with water. The precipitate is subjected to chromatography on silica using chloroform-methanol (95:5). The initial eluant fractions are combined, evaporated and crystallized from chloroform-methanol to give isomer L of the title compound; mp 290° C. and ir (nujol) 3350, 3290, 1640, 1692 and 1550 cm$^{-1}$. The latter eluant fractions are combined, evaporated and crystallized from acetone to give isomer M of the title compound; mp 200°–210° C. and ir (nujol) 3530, 3350, 3060, 1640, 1680, 1630 and 1540 cm$^{-1}$.

In the same manner but replacing 2-methylpropanol with an equivalent amount of benzaldehyde, the following compounds of formula I are obtained: the less polar (determined by silica gel chromatography) isomer L of α,α'-diphenyl-N,N'-dicyclohexyl-2,5,8,11,14,17-hexaoxo-1,4,7,10,13,16-hexaazacyclooctadecane-1,10-diacetamide, mp 330°–333° C. and ir (nujol) 3340, 3270, 3220, 3050, 1670, 1650, 1632, 1574 and 1546 cm$^{-1}$ and the corresponding more polar isomer M, mp 341°–343° C. and ir (nujol) 3340, 3250, 3090, 1665, 1620–1650, 1520 and 1562 cm$^{-1}$.

Similarly, replacing 2-methylpropanal with an equivalent amount of ethanal, pentanal or 4-phenylbutanal, the following compounds of formula I are obtained, respectively:

α,α'-dimethyl-N,N'-dicyclohexyl-2,5,8,11,14,17-hexaoxo-1,4,7,10,13,16-hexaazacyclooctadecane-1,10-diacetamide, α,α'-dibutyl-N,N'-dicyclohexyl-2,5,8,11,14,17-hexaoxo-1,4,7,10,13,16-hexaazacyclooctadecane-1,10-diacetamide and α,α'-di(3-phenylpropyl)-N,N'-dicyclohexyl-2,5,8,11,14,17-hexaoxo-1,4,7,10,13,16-hexaazacyclooctadecane-1,10-diacetamide.

In the same manner but replacing cyclohexylisonitrile with an equivalent amount of ethylisonitrile, cyclobutylisonitrile or methyl 3-isocyanobutanoate, the following compounds of formula I are obtained, respectively:

α,α'-dibenzyl-N,N'-diethyl-2,5,8,11,14,17-hexaoxo-1,4,7,10,13,16-hexaazacyclooctadecane-1,10-diacetamide, α,α'-diisopropyl-N,N'-dicyclobutyl-2,5,8,11,14,17-hexaoxo-1,4,7,10,13,16-hexaazacyclooctadecane-1,10-diacetamide and α,α'-diisopropyl-N,N'-di(2-methoxycarbonyl-1-methylethyl)-2,5,8,11,14,17-hexaoxo-1,4,7,10,13,16-hexaazacyclooctadecane-1,10-diacetamide.

EXAMPLE 2

α,α'-Di(1-phenylethyl)-N,N'-dicyclohexyl-2,5,8,11,14,17-hexaoxo-1,4,7,10,13,16-hexaazacyclooctadecane, 1,10-diacetamide (I; $R^1=CH(CH_3)C_6H_5$, $R^2$=cyclohexyl, $R^3$=H and A=Gly-Gly)

Cyclohexylisonitrile (0.654 g, 6 mmole) is added dropwise to a suspension at 0° to 5° C. of glycyl-glycyl-glycine (1.134 g, 6 mmole) and 2-phenylpropanal (2.68 g, 20 mmole) in anhydrous ethylene glycol (10 ml). After the addition is complete, the suspension is stirred at room temperature for 5 days. Water is added and the mixture is extracted with chloroform. The organic extract is dried (magnesium sulfate) and evaporated. The residue is subjected to chromatography on silica gel using chloroform-methanol (95:5) and the elutates are evaporated to give a residue of the two isomers of the title compound, mp 200° C. The residue is subjected to preparative thin layer chromatography on plates of silica gel using chloroform-isopropanol (95:5) to obtain the less polar isomer L of the title compound at $R_f$=0.413, mass spectrum: (m/e) 828(M$^+$), 810 and 792 and the more polar isomer M of the title compound at $R_f$=0.360, mass spectrum: (m/e) 828(M$^+$), 810 and 792.

In the same manner but replacing cyclohexylisonitrile with an equivalent amount of ethyl isocyanoacetate and replacing 2-phenylpropanal with an equivalent amount of 2-methylpropanal, N,N'-di(ethoxycarbonylmethyl)-α,α'-diisopropyl-2,5,8,11,14,17-hexaoxo-1,4,7,10,13,16-hexaazacyclooctadecane-1,10-diacetamide, nmr(CDCl$_3$) 1.00 (broad d, J=6.5 H$_z$, 12H), 1.26(t, J=7 H$_z$, 6H) and 4.0–4.38(q, J=7 H$_z$, 4H), is obtained.

Similarly, replacing glycyl-glycyl-glycine with an equivalent amount of alanyl-valine, leucyl-phenylalanyl-alanine, glycyl-tryptophyl-asparaginyl-isoleucine or seryl-prolyl-tyrosyl-methionyl-valine, the following compounds of formula I are obtained, respectively:

cyclo[N-[1-(1-phenylethyl)-2-cyclohexylamino-2-oxo-ethyl]-alanyl-valyl-N-[1-(1-phenylethyl)-2-cyclohexylamino-2-oxo-ethyl]-alanyl-valyl], cyclo[N-[1-(1-phenylethyl)-2-cyclohexylamino-2-oxo-ethyl]-leucyl-phenylalanylalanyl-N-[1-(1-phenylethyl)-2-cyclohexylamino-2-oxo-ethyl]-leucyl-phenylalanyl-alanyl], cyclo[N-[1-(1-phenylethyl)-2-cyclohexylamino-2-oxo-ethyl]-glycyl-tryptophyl-asparaginyl-isoleucyl-N-[1-(1-phenylethyl)-2-cyclohexylamino-2-oxo-ethyl]-glycyl-tryptophyl-asparaginyl-isoleucyl] and cyclo[N-[1-(1-phenylethyl)-2-cyclohexylamino-2-oxo-ethyl]-seryl-prolyl-tyrosyl-methionyl-valyl-N-[1-(1-phenylethyl)-2-cyclohexylamino-2-oxo-ethyl]-seryl-prolyl-tyrosyl-methionyl-valyl].

We claim:

1. A process for preparing a cyclopeptide of formula I

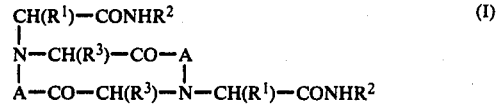

in which A is a peptide residue having one to four amino acid residues wherein said amino acid residues have a side chain selected from the group consisting of hydrogen and lower alkyl; $R^1$ is lower alkyl, phenyl or phenyl(lower)alkylene; $R^2$ is lower alkyl, cyclo(lower)alkyl or lower alkoxycarbonyl(lower)alkylene; and $R^3$ is a amino acid side chain selected from the group consisting of hydrogen and lower alkyl, which comprises:
  condensing together an aldehyde of formula $R^1CHO$ in which $R^1$ is as defined herein, an isonitrile of formula $R^2NC$ in which $R^2$ is as defined herein and a peptide of formula $H_2N$—CH($R^3$)—CO—A—OH in which A and $R^3$ are as defined herein.

2. The process as claimed in claim 1 wherein $R^1$, $R^2$, and $R^3$ are as defined therein, and A is a peptide residue having two amino acid residues wherein said amino acid residues have a side chain selected from the group consisting of hydrogen and lower alkyl.

3. The process as claimed in claim 1 wherein $R^1$ and $R^2$ are as defined therein, $R^3$ is hydrogen and A is Gly-Gly.

* * * * *